United States Patent [19]
Yang et al.

[11] Patent Number: 6,143,740
[45] Date of Patent: Nov. 7, 2000

[54] HEREGULIN ANTAGONISTS AND METHODS FOR THEIR USE

[75] Inventors: Dajun Yang, Gaithersburg, Md.; Shaomeng Wang, McLean, Va.; Alan P. Kozikowski, Princeton, N.J.; Marc E. Lippman, Bethesda, Md.

[73] Assignee: Georgetown University, Washington, D.C.

[21] Appl. No.: 09/308,396

[22] PCT Filed: Nov. 19, 1997

[86] PCT No.: PCT/US97/21474

§ 371 Date: Aug. 16, 1999

§ 102(e) Date: Aug. 16, 1999

[87] PCT Pub. No.: WO98/21956

PCT Pub. Date: May 28, 1998

Related U.S. Application Data

[60] Provisional application No. 60/031,368, Nov. 19, 1996.

[51] Int. Cl.$^7$ .................. A61K 31/33; A61K 31/495; C07K 1/00; C07K 16/00
[52] U.S. Cl. .................. 514/183; 514/255; 540/575; 544/374; 530/350; 530/389.3
[58] Field of Search .................. 540/575; 514/183, 514/255; 544/374; 530/350, 389.3

[56] References Cited

U.S. PATENT DOCUMENTS

| | | | |
|---|---|---|---|
| 3,796,798 | 3/1974 | Lancini et al. | 514/255 |
| 3,925,366 | 12/1975 | Marsili et al. | 424/244 |
| 4,585,589 | 4/1986 | Malabarba et al. | 260/239.3 |
| 4,590,185 | 5/1986 | Marsili et al. | 514/183 |
| 4,681,938 | 7/1987 | Traxler | 540/458 |
| 4,774,237 | 9/1988 | Ueno et al. | 514/183 |
| 5,095,108 | 3/1992 | Konstantinova et al. | 540/458 |
| 5,367,060 | 11/1994 | Vandlen et al. | 530/399 |

OTHER PUBLICATIONS

Database Caplus on STN, Abstract No. 1997:684761 for Dinda, S., et al., "Inhibition of Proliferation of T47D human breast cancer cells: alterations in progesterone receptor and p53 tumor suppressor protein", *Mol. Cell, Biochem.*, 175 (1 & 2), pp. 81–89, (1997).

Primary Examiner—Deborah C. Lambkin
Attorney, Agent, or Firm—Schwegamn, Lundberg, Woessner & Kluth, P.A.

[57] ABSTRACT

The invention provides a method of inhibiting cancer cell growth, and thereby of treating cancer comprising administering to a mammal afflicted with cancer an effective amount of the compound of formula (I), wherein the variables of $R_1$, and $R_2$ have the meanings defined in the specification. The present invention also provides novel compounds of formula (I) as well as novel pharmaceutical compositions and intermediates useful for preparing compounds of formula (I). The figure illustrates the structure and binding activity of compounds of the invention and some of the rifamycin analogs.

| Compounds | $R_1$ = |
|---|---|
| A1 | —OH |
| A2 | —OH |
| A3 | —OH |
| A4 | —OH |
| A5 | —OH |
| A6 | —OH |
| A7 | —OH |
| A8 | —CH$_2$—C(=O)—N(CH$_2$—CH$_3$)$_2$ |

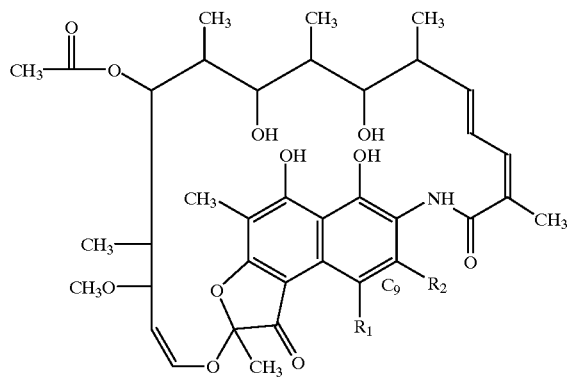
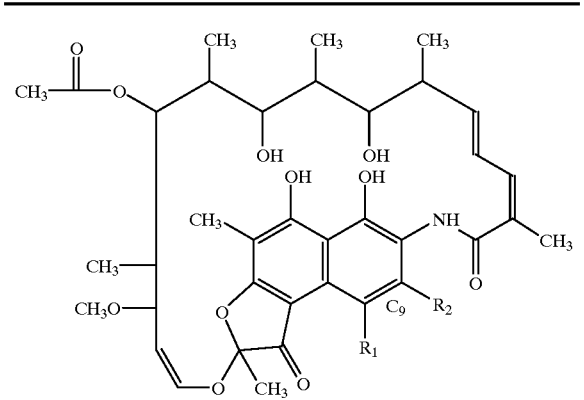
A5
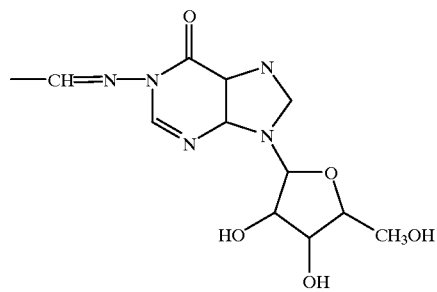
A6
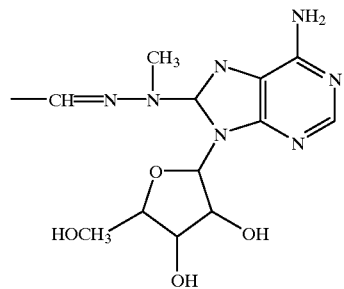
A7
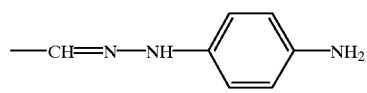
A8 —H
| Compounds | IC$_{50}$ (1) | IC$_{50}$ (2) |
|---|---|---|
| A1 | 10 uM | 1 uM |
| A2 | 10 uM | 3 uM |
| A3 | 10 uM | 3 uM |
| A4 | 50 uM | 5 uM |
| A5 | >500 uM | >50 uM |
| A6 | >500 uM | >50 uM |
| A7 | >200 uM | >50 uM |
| A8 | >500 M | >50 uM |
10 Claims, 14 Drawing Sheets

| Compounds | $R_1 =$ | $R_2 =$ | $IC_{50}$ (1) | $IC_{50}$ (2) |
|---|---|---|---|---|
| A1 | -OH | (3-hydroxyphenyl-methyl-dimethylpiperidine-N=CH-) | 10 uM | 1 uM |
| A2 | -OH | (2-hydroxyphenyl-methyl-dimethylpiperidine-N=CH-) | 10 uM | 3 uM |
| A3 | -OH | (adamantyl-N=CH-) | 10 uM | 3 uM |

| | | | | |
|---|---|---|---|---|
| A4 | -OH |  —CH=N-N< | 50 uM | 5 uM |
| A5 | -OH |  —CH=N-N | >500 uM | >50 uM |
| A6 | -OH |  —CH=N-N | >500 uM | >50 uM |
| A7 | -OH |  —CH=N-NH— | >200 uM | >50 uM |
| A8 |  | -H | >500 M | >50 uM |

New Compounds/Analogues

| Compounds | R₁ | R₂ |
|---|---|---|
| A9 | -OH | —CH=N-N(piperidine with H₃C groups and N—CH₂Ph) |
| A10 | -OH | -CH=NOCH₂Ph₂ |
| A11 | -OH | -CH=NO(CH₂)₄CH₃ |

| | | |
|---|---|---|
| A12 | -OH | -CH=NO(CH$_2$)$_3$Ph |
| A13 | -OH | -CH=NO(CH$_2$)$_8$CH$_3$ |
| A14 | -OH | -CH=NO(CH$_2$)$_9$CH$_3$ |
| A15 | -OH | -CH=NO(CH$_2$)$_{10}$CH$_3$ |
| A16 | -OH |  |
| A17 | -OH |  |

| | | |
|---|---|---|
| A18 | -OH | -CH=N-N⟨piperazine-N-CH₃⟩ |
| A19 | -OH | -CH=N-N⟨piperidine⟩ |
| A20 | -OCH₂CON(CH₂CH₃)₂ | -H |
| A21 | Monosodium Rifamycin | |
| A22 | Geldampicin (no structure) | |

FIG. 8A

HEREGULIN ANTAGONISTS AND METHODS FOR THEIR USE

Provisional Application No. 60/031,368, filed Nov. 19, 1996. This application is a 371 of PCT/US97/21474, filed Nov. 19, 1997.

BACKGROUND OF THE INVENTION

Members of the EGF receptor family, including the EGFR, erbB-2/neu, erbB-3 and erbB-4 genes are overexpressed in at least 60–70% of human breast cancers. Targeted inhibition of the erbB receptor(s) with monoclonal antibodies, immunotoxins or antisense oligonucleotides has been reported and some have reached early phase clinical trials. Several major therapeutic limitations are associated with these approaches, including large molecule size, poor tissue penetration, delivery, and host immune responses.

Attempts to isolate a ligand for erbB-2/neu led to the discovery of gp30, or heregulin (HRG or NDF) (Lupu et al., Science, 256:1205–1210, 1992; Holmes et al., Science 256:1205–1210, 1992; Peles et al., Cell, 69:205–216, 1992). HRG contains an EGF-like domain which is effective to bind and stimulate of p185$^{erbB}$ phosphorylation. The EGF-like domain of HRG contains six cysteine residues that are characteristic of the EGF family of growth factors, but HRG does not bind to EGF receptors (Holmes et al., Science 256:1205–1210, 1992; Peles et al., Cell, 69:205–216, 1992; Falls et al., Cell, 72:801–815, 1993; Marchionni et al., Nature, 362:312–318, 1993; Peles et al., Bioessays, 15:815–824, 1993). Both erbB-3 and erbB-4 are receptors for HRG (Plowman et al., Nature, 366:473–475, 1993; Carraway et al., Cell, 78:5–8, 1994; Tzahar et al., J. Biol. Chem. 269:25266–25233, 1994; Carraway et al., J. Biol. Chem. 269:14303–14306, 1994; Kita et al., FEBS Lett., 349:139–143, 1994).

The heregulins (also called neuregulins, NDF, GGF, and ARIA) belong to a family of membrane-bound or secreted proteins produced by neurons and mesenchymal cells. They have multiple effects on a wide range of cell types. Lemke, G. Mol. Cell. Neurosci., vol. 7, 2996, 247–262; and D. Zhang, Proc. Natl. Acad. Sci. USA, vol. 94, 1997, 9562–9567.

It is generally recognized now that the homodimers of erbB-4 are biologically active, whereas the signaling of HRG through erbB-3 is dependent on heterodimerization with other erbB-3 receptors, predominantly the erbB-2 (Carraway et al., Cell, 78:5–8, 1994; Sliwkowski et al., J. Biol Chem. 269:146; Alimandi et al., Oncogene 1995 10(9):1813–21; Chen et al., J. Biol. Chem. 271:7620, 1996).

Expression of HRG has been demonstrated in human breast cancers (Normanno et al., Int. J. Onco. 2:903, 1993; Normanno et al., Breast Cancer Res Treat 1995, 35(3):293–7) and HRG might perform a role in autocrine growth regulation (Carraway et al., Cell, 78:5–8 (1994), progression to estrogen-independent growth and increased tumorigenicity of breast cancer cells (Pietras et al., Oncogene, 1995, 15:10(12):2435–46). Immunostaining studies show that erbB-3 is overexpressed in breast cancer (Lemoine et al., Br. J. Cancer, 66:1116–1121, 1992; Quinn et al., Histopatho., 25:247–252, 1994; Gasparini et al., Eur. J. Cancer, 30A:16–22, 1994), and others (Simpson et al., Br. J. Cancer, 71:758–762, 1995; Myers et al., J. Natl. Cancer Inst. 86:1140–1145, 1994). The expression of erbB-4 is elevated in breast cancer cell lines (Plowman et al., Proc. Natl. Acad. Sci. USA, 90:1746–1750, 1993), and is overexpressed in invasive ductal carcinoma and DCIS of breast but not in the nearby normal breast cells.

Thus, a need exists for specific antagonists of HRG which can function as effective inhibitors of cancer cell growth.

SUMMARY OF THE INVENTION

The present invention provides a therapeutic method to inhibit cancer cell growth comprising administering to a mammal (i.e. a human) in need of such therapy, an amount of a compound of formula (I):

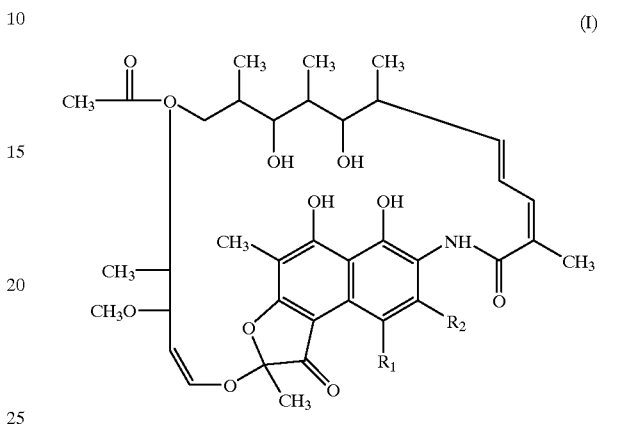

wherein $R_1$ is OH or —$CH_2C(O)N((C_1-C_4)alkyl)_2$;

$R_2$ is —CH=N—N($R_7$)($R_8$), —CH=NO(($C_1-C_{12}$) alkyl), —CH=NOCH(phenyl)$_2$, —CH=NO(CH$_2$)$_n$-phenyl, —CH=N—NHR$_9$, —CH=N—R$_{10}$

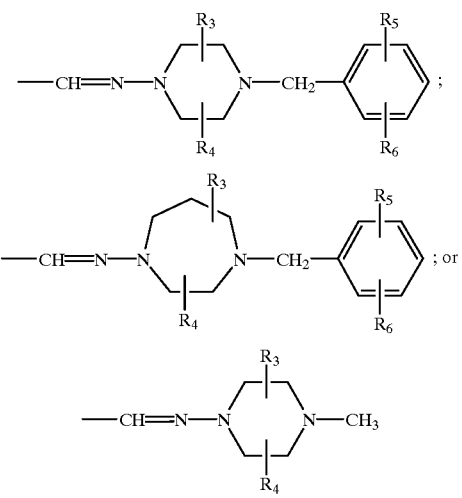

n is 1–6;

$R_3$ and $R_4$ are each independently H, ($C_1$–$C_4$)alkyl (preferably —CH$_3$), halo, halo($C_1$–$C_4$)alkyl, or ($C_5$–$C_7$)aryl optionally comprising 1–2 N, S or non-peroxide O and optionally substituted with ($C_1$–$C_4$) alkyl or halo;

$R_5$ and $R_6$ are each independently H, OH, —NH$_2$, —C(O) OH or —C(O)NH$_2$;

$R_7$ is H or ($C_1$–$C_4$)alkyl; and $R_8$ is a bi- or tricyclic ring, said ring comprising 7 to 10 carbons (preferably adamantane), optionally comprising one or more (e.g., 1–4) heteroatoms selected from S, N or non-peroxide O, said ring optionally substituted with ($C_1$–$C_4$)alkyl, halo or halo($C_1$–$C_4$)alkyl; or $R_7$ and $R_8$ together with the nitrogen to which they are attached form a ring comprising 10 to 20 carbons (preferably 17), optionally comprising one or more (e.g., 1–4) heteroatoms selected from S, N or non-peroxide O, said ring optionally substituted with ($C_1$–$C_4$)alkyl, halo or halo($C_1$–$C_4$) alkyl;

$R_9$ is ($C_1$–$C_4$)alkyl, a peptidyl residue of naturally occuring amino acid, or a di-, tri-, or tetra-peptide; and $R_{10}$ is a a piperazin-1-yl ring, optionally substituted on carbon with one or two substituents selected from the values defined for $R_3$ and $R_4$, and optionally substituted at the 4-position with a group $R_{11}$, wherein $R_{11}$ is ($C_1$–$C_4$)alkyl, phenyl, benzyl, a peptidal residue of a naturally occuring amino acid, or a di-, tri-, or tetra-peptide;

or a pharmaceutically acceptable salt thereof;

wherein said amount is effective to inhibit growth of said cancer cells.

In a preferred embodiment, the cancer cells are solid tumor cells such as breast cancer cells.

The present invention also provides a pharmaceutical composition comprising an effective amount of a compound of formula (I) in combination with a pharmaceutically acceptable carrier.

The invention also provides novel compounds of formula (I), as well as intermediates and processes disclosed herein as useful for preparing compounds of formula (I).

The invention also provides a compound of formula (I) for use in medical therapy (preferably for use in inhibiting cancer cell growth).

Representative compounds of formula (I) have been shown to possess activity as heregulin antagonists. Thus, compounds of formula (I) may be useful for treating diseases or conditions in which cell signaling by heregulin(s) or their receptor(s) is implicated and antagonism of said cell signaling is desired. Accordingly, the invention also provides a method for antagonizing the actions of a heregulin or its receptor by contacting (in vivo or in vitro) said receptor with an effective amount of a compound of formula (I). The invention also provides a method for treating a disease (i.e. cancer) or condition in which cell signaling by a heregulin or its receptor(s) is implicated, comprising administering to a mammal (human) afflicted with said dieseas or condition, an antagonistically effective amount of a compound of formula (I).

The invention also provides, a compound of formula (I) for use in antagonizing the actions of heregulin or its receptor, as well as a compound of formula (I) for use in treating a disease (i.e. cancer) or condition in which cell signaling by heregulin or its receptor(s) is implicated.

The invention also provides the use of a compound of formula (I) to prepare a medicament useful for treating a disease (i.e. cancer) or condition in which cell signaling by heregulin or its receptor(s) is implicated.

DETAILED DESCRIPTION OF THE INVENTION

Certain analogs of rifamycin have been discovered which are specific antagonists of HRG in receptor binding competition, HRG-induced phosphorylation and HRG-dependent cell proliferation assays. Molecular modeling investigations showed that rifamycin analogues of the present invention can be superimposed using their large ring backbone as the template. Structural differences exist at the $C_9$ position, where different substituents can be attached.

It is clear that this site plays an important role in their antagonist activity, since compounds with different substituents at this site showed activities from virtually inactive to fairly potent (10–100 fold difference in binding, phosphorylation, and HRG-dependent growth inhibition assays). Molecular modeling studies, comparing the structures of rifamycin analogues to the pharmacophore model derived from the HRG 3D structure showed that substituents at this site reside in the region as occupied by residues 177 to 180 (Ser-His-Leu-Val) in HRG. Residues 177–180 have been shown to play an important role in HRG binding to its receptor (Barbacci et al., *J. Bio. Chem.* 1995; 270(16) 9585–9). Deletion of residues 177 to 181 makes the ligand completely inactive. Replacement of residues 177 and 178 by an acetyl group decreases the binding affinity of HRG to its receptor by more than 50-fold (Barbacci et al., *J. Bio. Chem.* 1995; 270(16)9585–9).

Figure 7A:
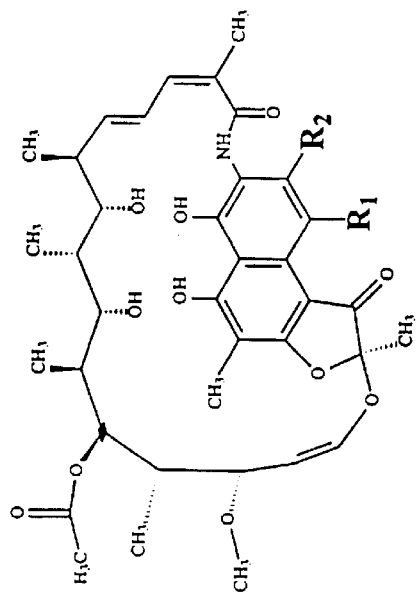
FIG. 7 Illustrates the structure of compounds of the invention and some other rifamycin analogs.
Figure 7B:
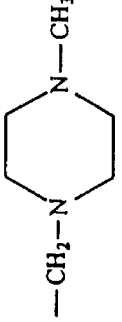
Figure 7B:
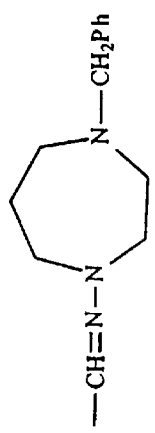
Figure 8B:
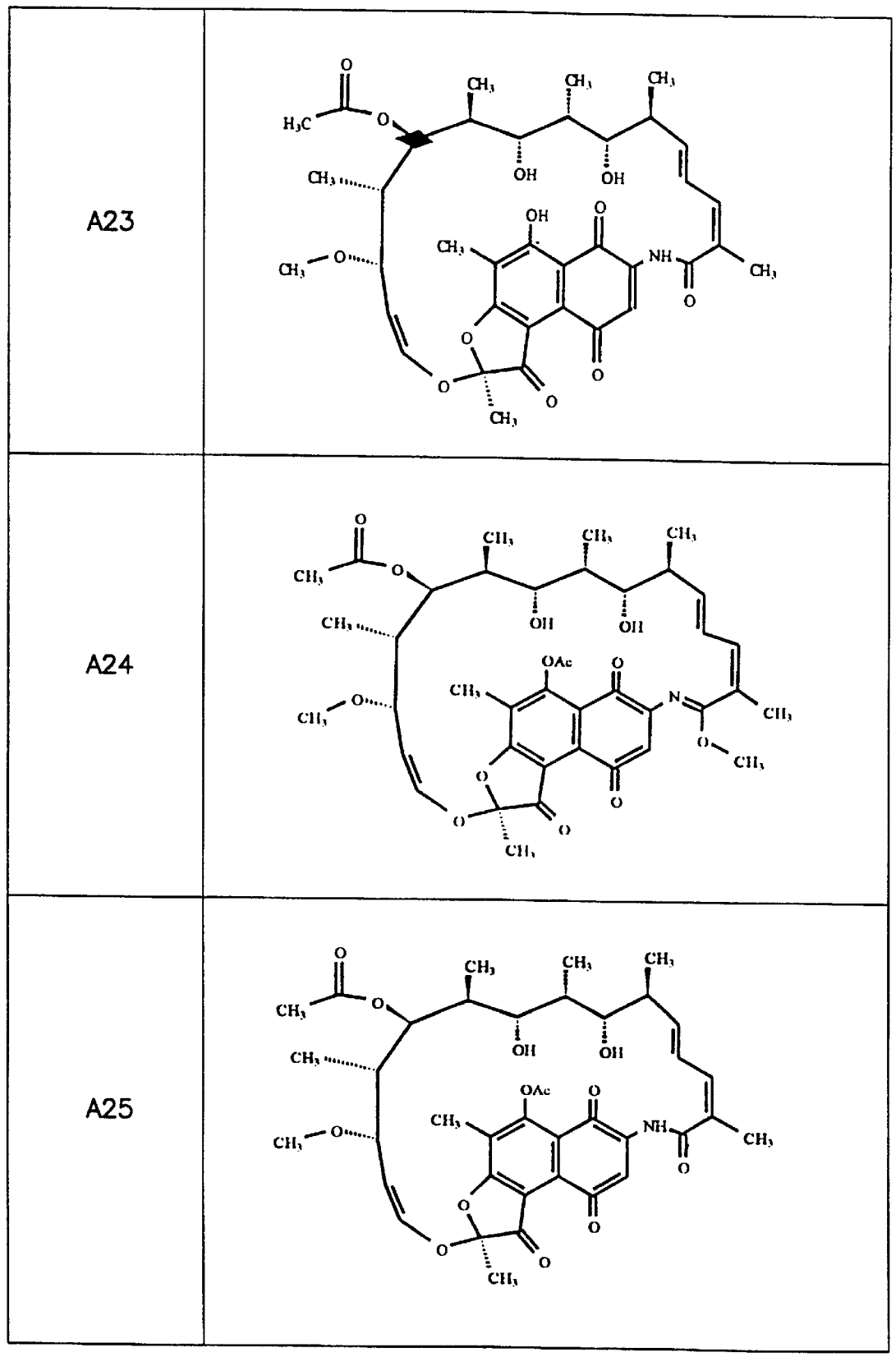
FIG. 8 Illustrates the structure of compounds of the invention and some other rifamycin analogs.
Figure 8C:
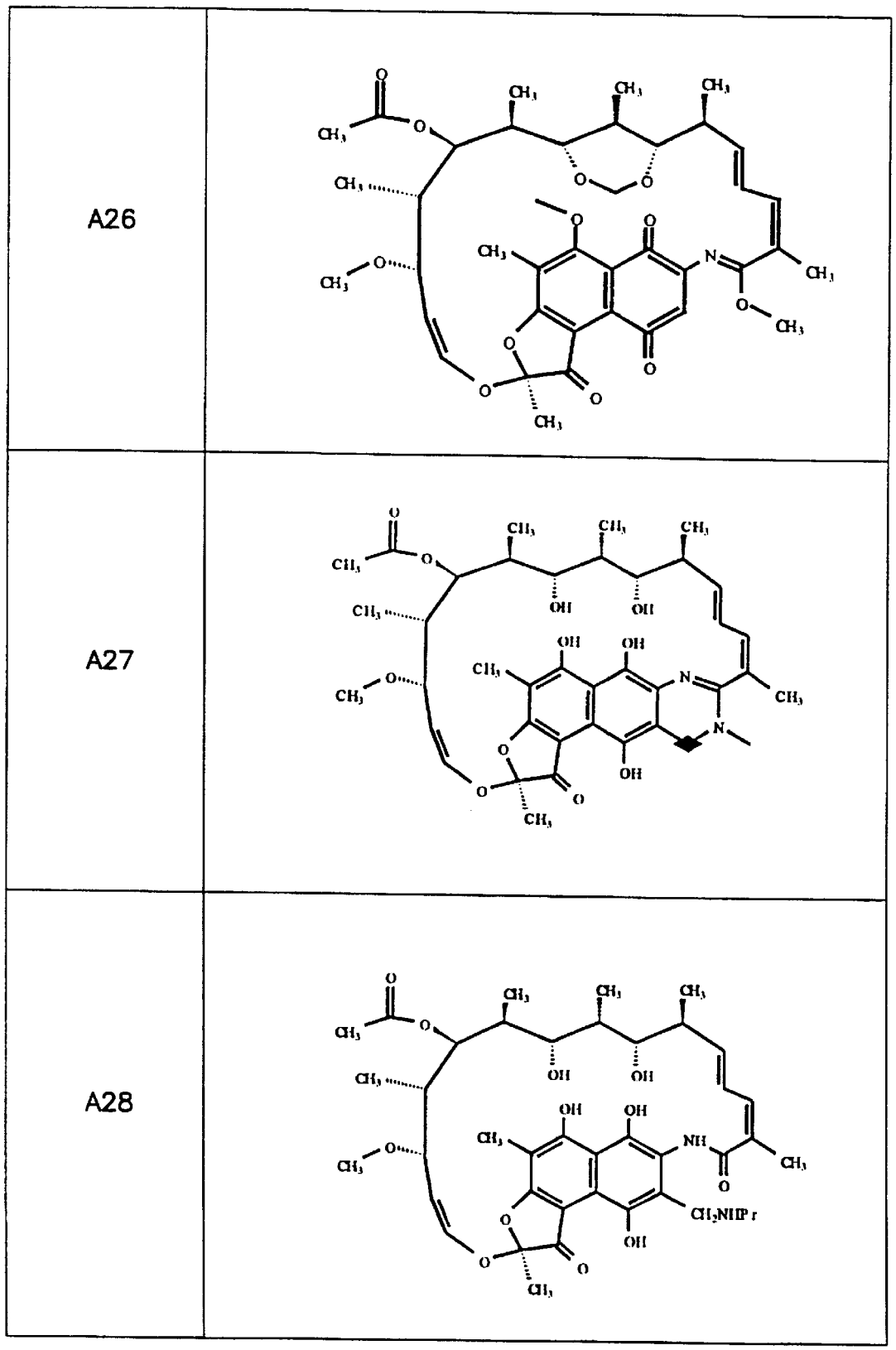

The structure-activity relationships of rifamycin analogues also indicates the importance of this region (FIGS. 6 and 7). For example, compounds with a bulky hydrophobic substituent at this site, such as compounds A3 and A4, display fairly good activities, while compounds A5–A7, which have a hydrophilic group at this site, are virtually inactive. Molecular modeling studies suggested that the hydrophobic group at this site mimics the hydrophobic residues Leu 179 and perhaps Val 180. Modeling studies of compounds A1 and A2 showed that 1,5-dimethyl piperazine mimics the hydrophobic residue Leu 179 and the hydroxyl benzyl group mimics His178 and perhaps Ser 177 in HRG.

Specific and preferred values listed below for radicals, substituents and ranges, are for illustration only; they do not exclude other defined values or other values within defined ranges for the radicals and substituents.

Specifically, $R_2$ can be

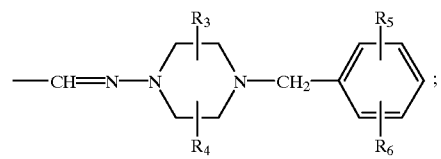

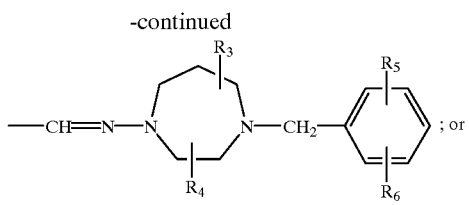

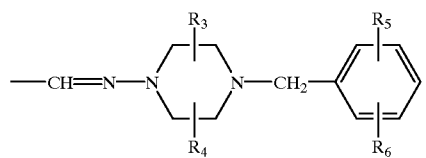

More specifically, $R_3$ and $R_4$ can each be —$CH_3$; $R_5$ can be OH; and $R_6$ can be H.

A specific group of compounds are compounds of formula (I) wherein $R_5$ and $R_6$ are independently H, —$NH_2$, —$C(O)$OH or —$C(O)NH_2$. Another specific group of compounds are compounds of formula (I) wherein $R_2$ is —CH=N—N$(R_7)(R_8)$ or —CH=NO$(CH_2)_n$-phenyl. Another specific group of compounds are compounds of formula (I) wherein $R_2$ is —CH=N—NHR$_9$. Another specific group of compounds are compounds of formula (I) wherein $R_2$ is —CH=N—R$_{10}$. Another specific group of compounds are compounds of formula (I) wherein $R_9$ is a peptide residue selected from the group consisting of -Val-Leu-His-Ser, -Leu-His-Ser, -Val-Leu-His, -Val-Leu, -Leu-His, -His-Ser, -Asn-Ser-Asp-Ser, -Asn-Ser-Asp, -Asn-Ser, or -Ser-Asp-Ser. Another specific group of compounds are compounds of formula (I) wherein $R_1$ is a peptide residue selected from the group consisting of -Val-Leu-His-Ser, -Leu-His-Ser, -Val-Leu-His, -Val-Leu, -Leu-His, -His-Ser, -Asn-Ser-Asp-Ser, -Asn-Ser-Asp, -Asn-Ser, or -Ser-Asp-Ser.

A preferred group of compounds are compounds of formula (I) wherein $R_1$ is OH.

Another preferred group of compounds are compounds of formula (I) wherein $R_2$ is Based upon modeling studies, the hydrophobic residue Leu 179 can be mimiced by adding small hydrophobic groups, such as methyl, trifluoromethyl, ethyl, n-propyl, isopropyl, n-butyl, t-butyl, phenyl, fluorine, chlorine and bromine on the piperazine ring of such an $R_2$. Additionally, small, hydrophilic groups, such as hydroxy, amino, carboxy and aminocarbonyl, may optionally be substituted on the phenyl ring of such an $R_2$. More than one substituent can be attached to the piperazine and phenyl rings in a compound. Thus, modifications can be made at positions 1,2,4,5 of said piperazine ring and at positions 1', 2', 3', 4', 5' of said phenyl ring:

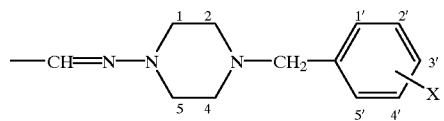

Previous studies have shown that this site also controls the specificity of the binding of HRG or EGF to their receptor. Therefore, tetra-, tri-, di- or mono-peptide segments can be attached to the core of rifamycin at this site, with the sequence either from HRGs (residues 177–180, SHLV) or EGF(residues 1–4, NSDS) to yield compounds with specific antagonist activity against HRG receptor or EGFR.

The compounds of formula (I) may be synthesized using 3-formylrifamycin O-n-octyloxime (compound I of Scheme 1), which is hydrolyzed under metal ion catalysis to afford the corresponding aldehyde. For example, either molybdenum or iron carbonyl can be used to effect the necessary conversion. Reaction of the aldehyde (compound II in Scheme 1) with selected alkyl- and arylhydrazines to provide the corresponding hydrazones (compound III in Scheme 1). These reactions can be carried out under mild conditions employing p-toluenesulfonic acid as a catalyst in methylene chloride as the solvent. Detailed synthetic schemes for proposed compounds are shown in Schemes 1 and 2.

Scheme 1

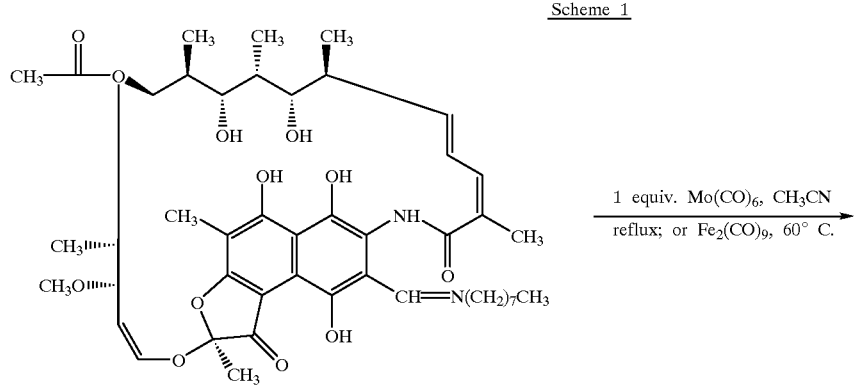

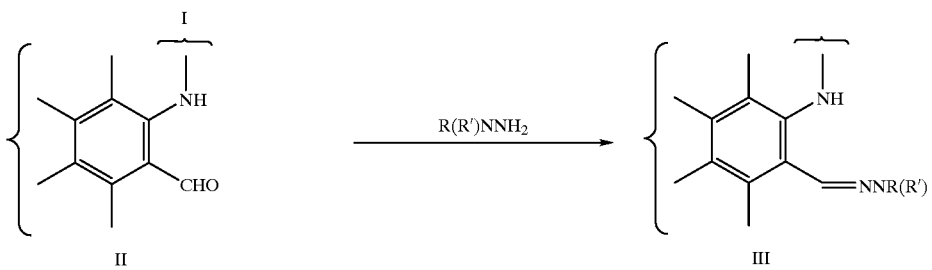

(See, Nitta et al., *Bull. Chem. Soc. Jpn*, 59, 2365, 1986; Nitta et al., *Bull. Chem. Soc. Jpn*, 57, 3357, 1984).

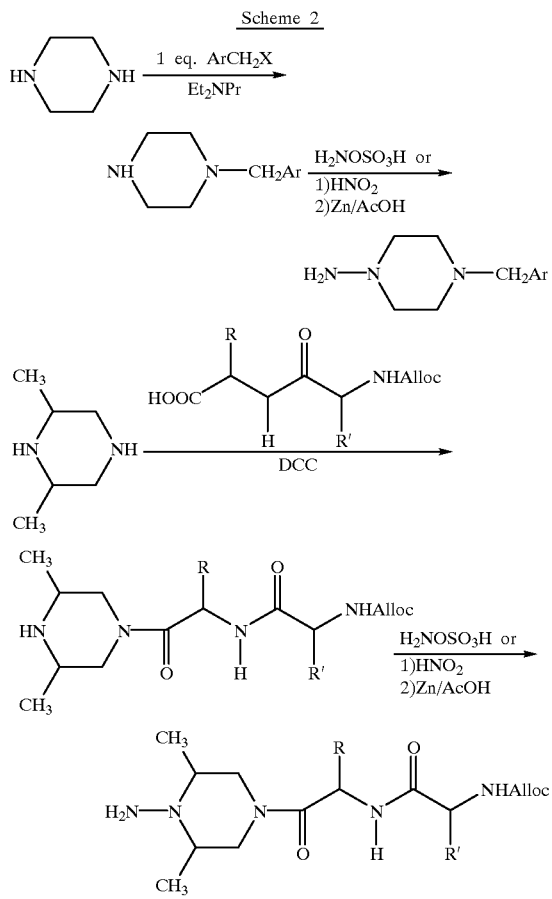

Scheme 2

(Where Alloc is —C(O)OCH$_2$CH=CH$_2$). See Gosl et l., *Org. Syn.* 43, 1, 1963; and Kunz et al., *Angew. Chem., Int. Ed. Engl.* 23, 436, 1984.

Pharmaceutically acceptable salts of the compounds of formula (I) are also an embodiment of the invention. Pharmaceutically acceptable salts of acids may be formed using organic or inorganic bases, such as NaOH, Na$_2$(CO$_3$), NaHCO$_3$, KOH and the like. Amine salts may be prepared from organic or inorganic acids, such as HCl, H$_2$SO$_4$, TsOH, citric acid, maleic acid, malic acid, tartaric acid and the like.

Peptidyl derivatives such as N-protected (i.e. NAc, NBz, etc.) Derivatives are also within the scope of the invention.

Although the compounds of formula (I) and/or their its salts may be administered as the pure chemicals, it is preferable to present the active ingredient as a pharmaceutical composition. The invention thus further provides the use of a pharmaceutical composition comprising one or more compounds of formula (I) and/or a pharmaceutically acceptable salt thereof, together with one or more pharmaceutically acceptable carriers therefor and, optionally, other therapeutic and/or prophylactic ingredients. The carrier(s) must be 'acceptable' in the sense of being compatible with the other ingredients of the composition and not deleterious to the recipient thereof.

Pharmaceutical compositions include those suitable for oral or parenteral (including intramuscular, subcutaneous and intravenous) administration. The compositions may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combination thereof, and then, if necessary, shaping the product into the desired delivery system.

Pharmaceutical compositions suitable for oral administration may be presented as discrete unit dosage forms such as hard or soft gelatin capsules, cachets or tablets each containing a predetermined amount of the active ingredient; as a powder or as granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art, e.g., with enteric coatings.

Oral liquid preparations may be in the form of, for example, aqueous or oily suspension, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservative.

The compounds may also be formulated for parenteral administration (e.g., by injection, for example, bolus injection or continuous infusion) and may be presented in unit dose form in ampules, pre-filled syringes, small bolus infusion containers or in multi-does containers with an added preservative. The compositions may take such forms as suspensions, solutions, or emulsions in oily or aqueous vehicles, and may contain formulatory agents such as suspending, stabilizing and/or dispersing agents. Preferable, the liquid carrier is a non-alkaline solution. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in Fisher et al. (U.S. Pat. No. 4,788,603) or Bawas et al. (U.S. Pat. Nos.4,931,279, 4,668,504 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122, 4,383,529, or 4,051,842.

Compositions suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described compositions can be adapted to provide sustained release of the active ingredient employed, e.g., by combination thereof with certain hydrophilic polymer matrices, e.g., comprising natural gels, synthetic polymer gels or mixtures thereof.

The pharmaceutical compositions according to the invention may also contain other adjuvants such as flavorings, coloring, antimicrobial agents, or preservatives.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided. e.g., into a number of discrete loosely spaced administrations; such as multiple inhalations from an insufflator or by application of a plurality of drops into the eye.

The following examples are intended to illustrate but not limit the invention.

EXAMPLES

Example I
In vitro Biological Activities and Specificities on Human Breast Cancer Cells The ability of compounds of the invention to inhibit cancer cell growth can be measured using highly malignant human MDA-231 breast cancer cells, which secrete HRG. Previous studies have shown that the growth of these cells can be blocked by neutralizing antibody (Lupu et al., *Breast Cancer Res. & Treat.* 1996, 38:57–66). SKOV-3 cells, which do not response to HRG or HRG-PE toxins, can be used as a negative control. The HRG can be transfected into the MCF-7 cells using techniques which are known in the art, for example, see Tang et al., *Cancer Res., July* 1996.

Figure 4:
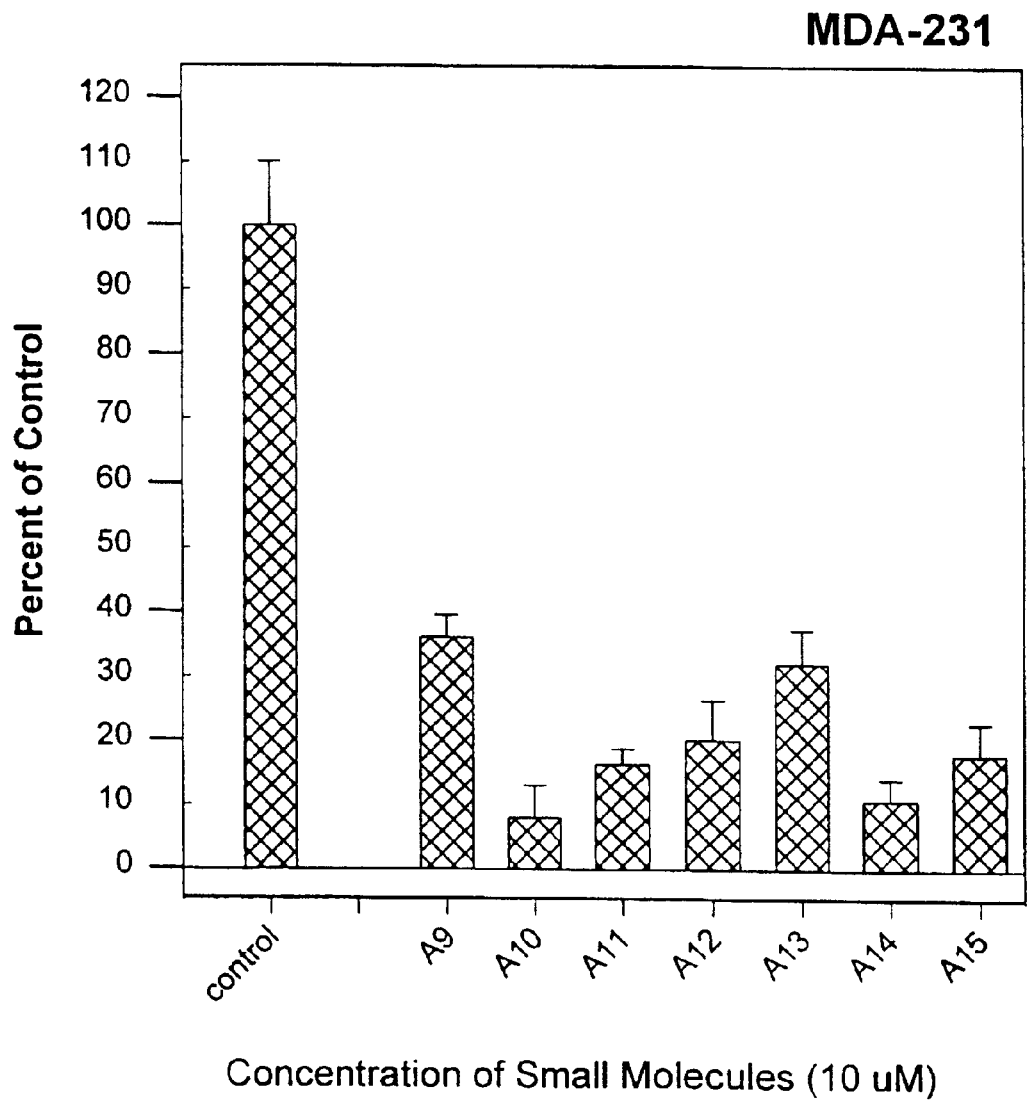
FIG. 4 illustrates the inhibition of human breast cancer cell proliferation by compounds of the invention.

Cell proliferation assays—The ability of compounds of the invention to kill cells can be directly measured using a soluble tetrazolium/formazan (XTT) assay, which is known in the art, for example, see Alley et al., *Cancer Res.*, 48:589–601, 1988. Data for representative compounds of the invention is provided in FIG. 4.

Figure 1A:
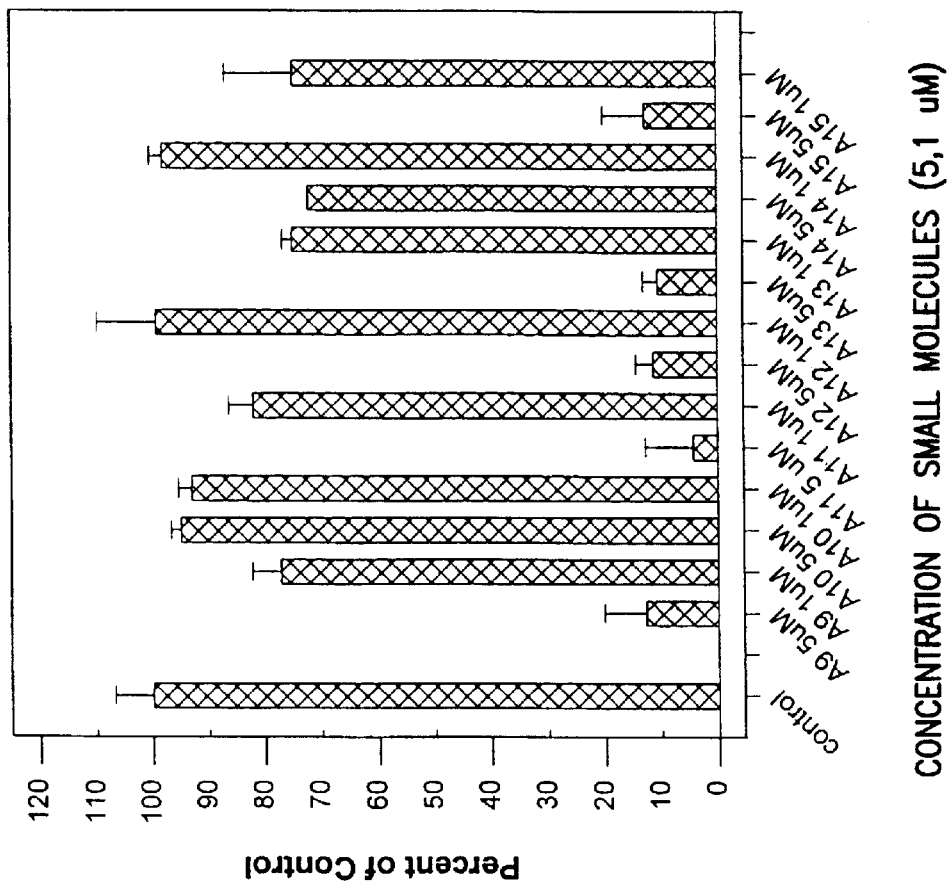
FIG. 1 illustrates the inhibition of 32D cell proliferation by compounds of the invention.
Figure 1B:
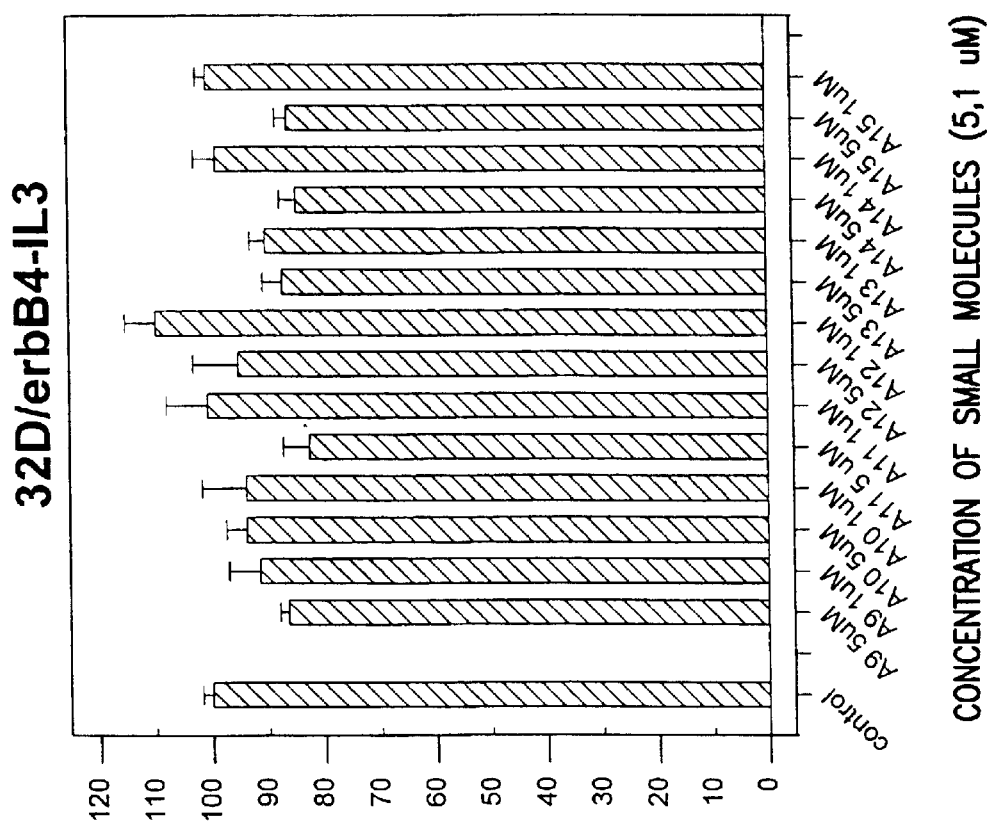
Figure 2A:
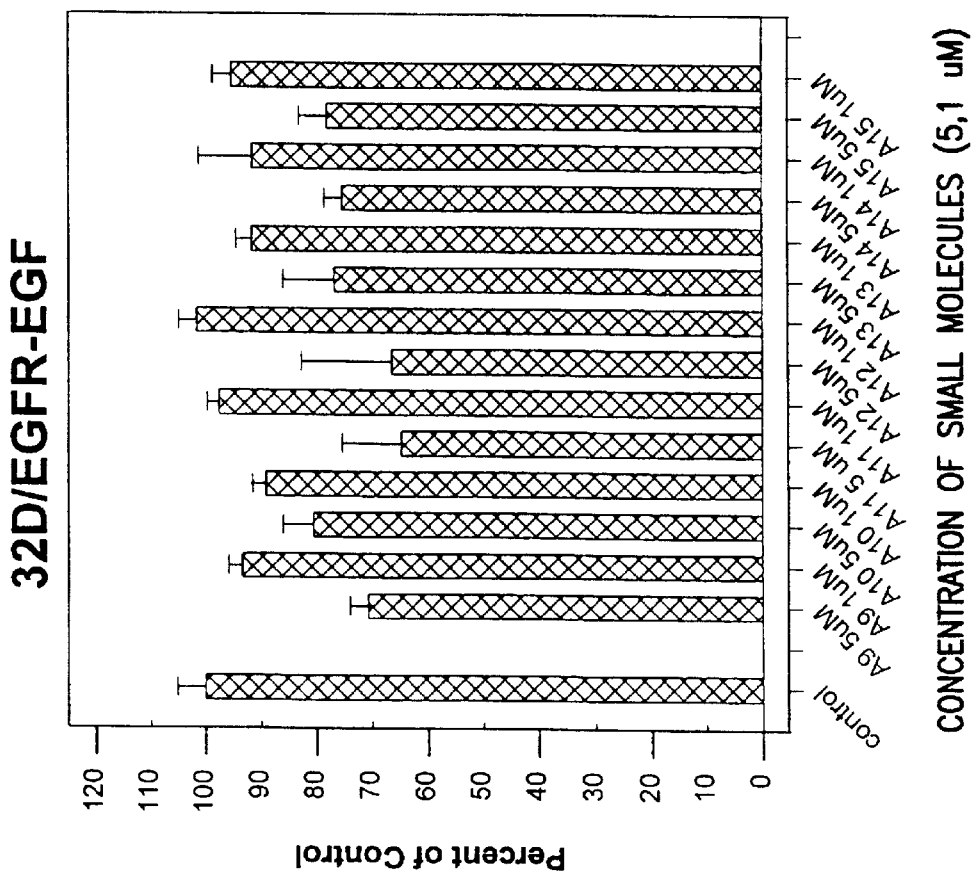
FIG. 2 illustrates the inhibition of 32D cell proliferation by compounds of the invention.
Figure 2B:
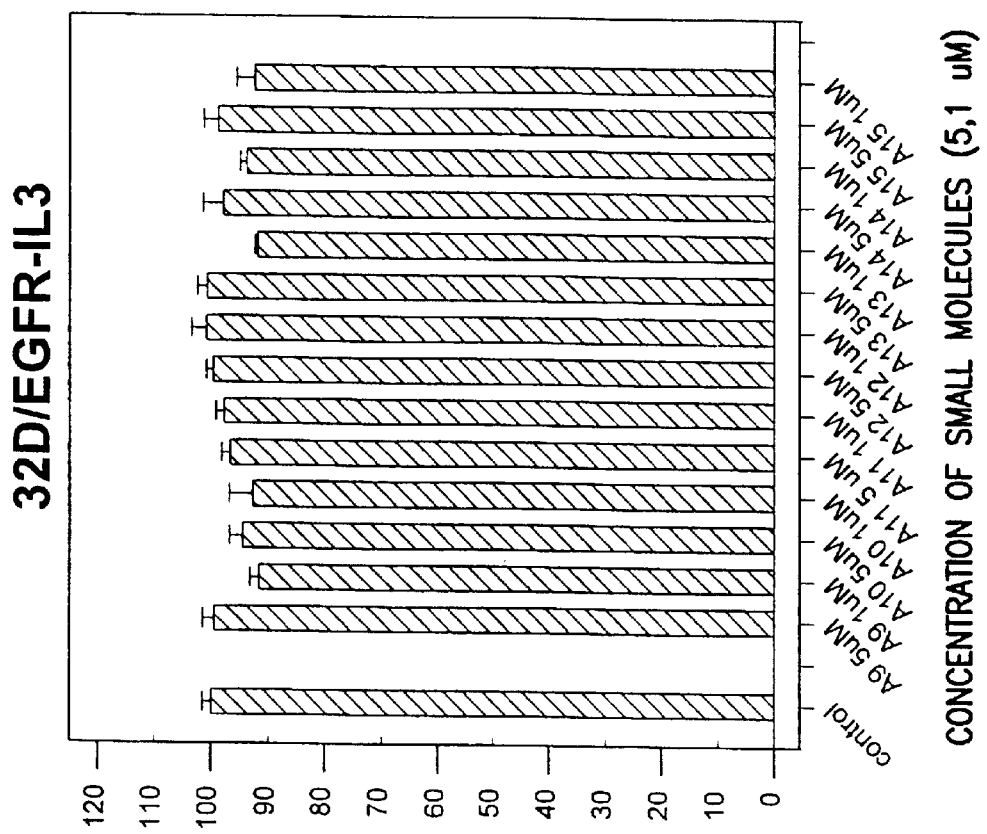

Inhibition of HRG-dependent cell proliferation—Since most human cancer cells express more than one of the erbB receptors and different heterodimerization might alter the binding affinity and/or internalization, it is difficult to define the exact correlation of the receptor expression and the antagonist activity of the small molecules. To overcome this difficulty, a 32D cell (murine, hematopoietic) model system, in which the 32D cells were transfected with erbB4 receptor, can be utilized. Wild-type 32D cells do not express any erbB receptors and are therefore strictly dependent on the IL-3 for survival and proliferation (Ruggiero et al., *FEBS*, 291, 203, 1991). 32t cells transfected with erbB-4 will proliferate in the presence of either HRG or IL-3. With this 32D cell model system, compounds of the invention can be tested for their antagonist activity and specificity in both HRG-dependent and HRG-independent growth. Active compounds such as A1 inhibit only the HRG-dependent cell growth in 32D/erbB-4 cells but not IL-3 stimulated growth in 32D or 32D/erbB-4 cells. Data for representative compounds of the invention is provided in FIGS. 1 and 2.

Figure 3A:
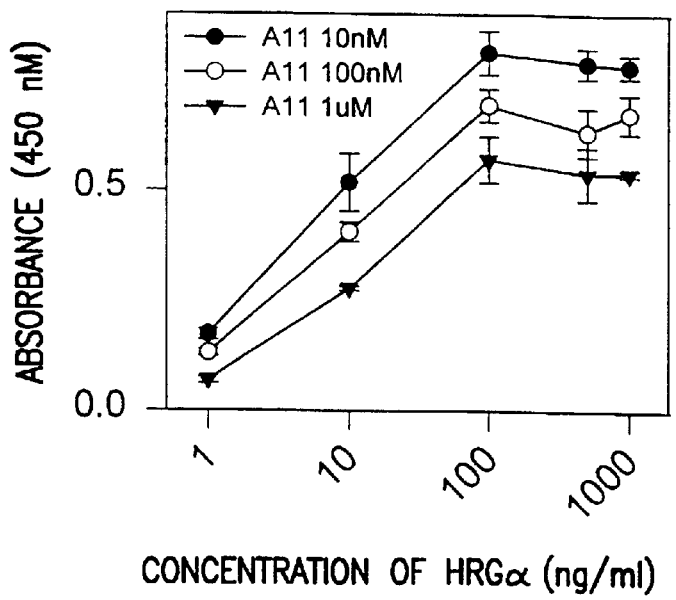
FIG. 3 shows the competeitive blockage of the effect of a compound of the invention by HRGα.
Figure 3B:
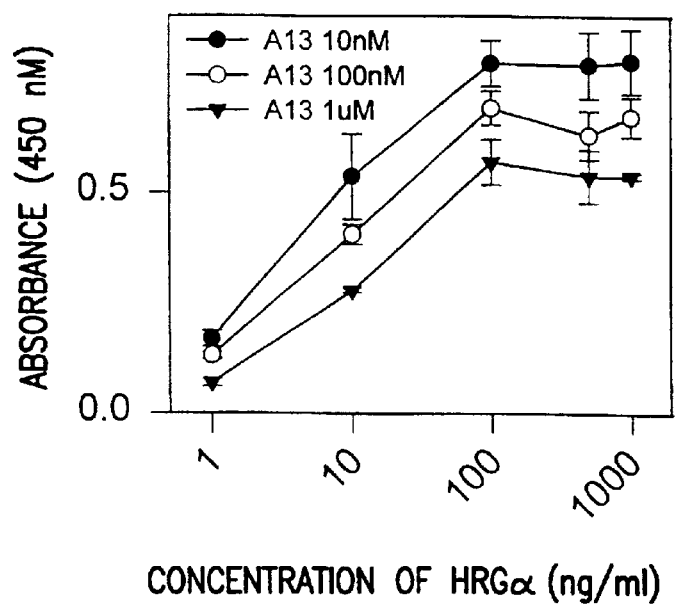

As illustrated in FIG. 3, addition of excess heregulin reduces the antiproliferative effects of compounds of the invention. This suggests that compounds of the invention are heregulin antagonists.

Example II
Colony-Formation in Soft-Agarose

Figure 5:
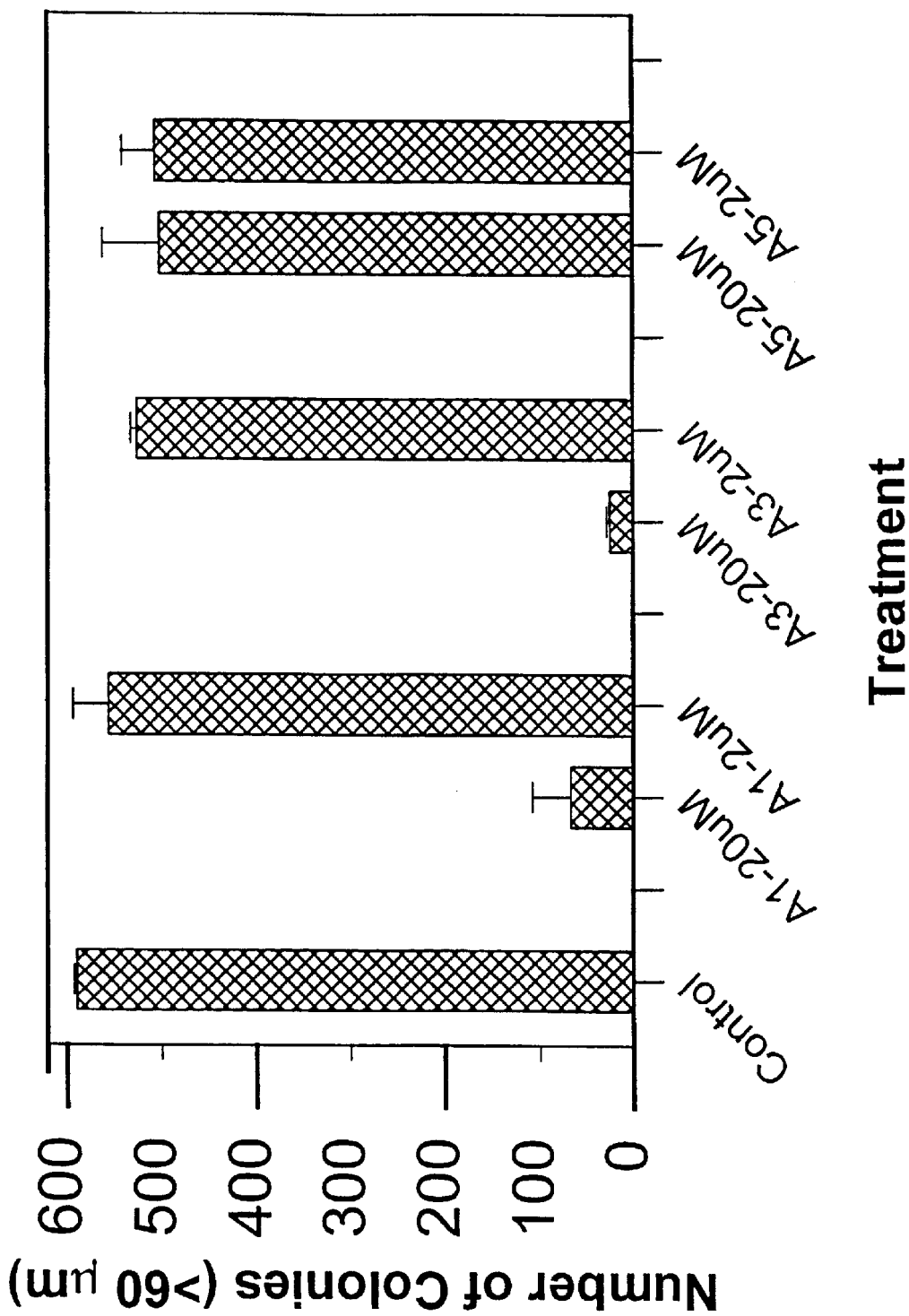
FIG. 5 illustrates the inhibition of soft-agar colony formation in breast cancer MDA-231 cells by compounds of the invention.
Figure 6A:
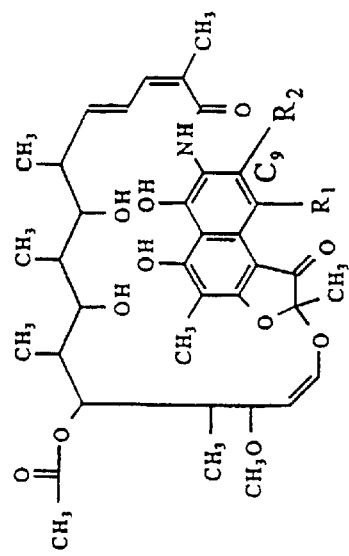
FIG. 6 Illustrates the structure and binding activity of compounds of the invention and some other rifamycin analogs.
Figure 6B:
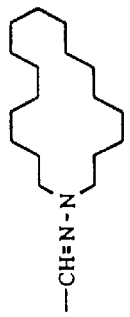
Figure 6B:
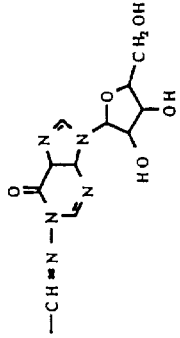
Figure 6B:
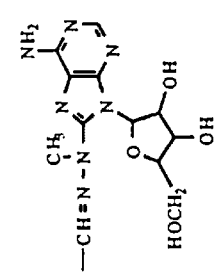
Figure 6B:
Figure 6B:
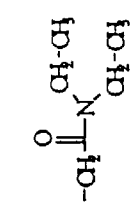

The soft-agar colony formation assay directly measures the transforming ability of a ligand and correlates well with in vivo tumorigenicity. This assay can be carried out using procedures similar to those described by: Yang et al., *Proc. Natl. Acad. Sci. USA*, 89, 2237–2241, 1992. Data for representative compounds of the invention is provided in FIG. 5.

Example III
Receptor Dimerization Assay and Kinase Activity Assay (Tyrosine Phosphorylation Assay)

The underlying mechanisms involving the inhibition of dimerization or inhibition of receptor tyrosine kinase activity can be explored in breast cancer cells as described by: Chen et al., J. Biol. Chem. 271:7620, 1996.

Inhibition of receptor binding—To investigate whether a compound can inhibit binding between HRG and its receptors, binding assays were performed using $^{125}$I labeled EGF domain of HRG-β1 (HED-β1). The binding affinity of iodine-labeled HED-β1 in T47D or MDA-453 cells was pre-determined. Unlabeled compounds were co-incubated with the radiolabeled ligand for 2 hours at 4° C., and the cells were washed 3 times with an ice-cold binding buffer. The labeled cells were lysed, and counted in a gamma-counter. Compounds that displaced more than 50% of labeled HED-β1 from the HRG-receptors were then re-examined in a dose-dependent manner.

Inhibition of HRG-induced tyrosine phosphorylation—Recombinant HRG-α1 and HRG-β1, which induce phosphorylation in a dose-dependent manner over a range of 0.01 nM to 1 uM in T47D cells, were prepared. The ability of compounds of the invention to block HRG-induced phosphorylation was tested by co-incubation with 10 nM HRG (maximal induction). (The results of inhibition studies performed with other rifamycin analogs are presented in FIGS. 6 and 7.)

The dose-dependent inhibition of compounds of the invention (A1 and A3) was determined in MDA-453 cells, and specificity was determined by incubating with the EGF in the EGFR receptor overexpressing cell line (MDA-468). These active compounds have no or very little effect on EGF-mediated signaling pathway, suggesting these active compounds, unlike herbimycin, probably do not function as general kinase inhibitors (Satoh et al., *J. Bio. Chem.*, 1992, 267(4):2537–41; *Current Med. Chem.*, 167–194, 1996).

Example IV

In vivo Antitumor Activities and Toxicities

Animal toxicity studies can be performed to determine the amount of a compound that can be given to animals for therapeutic studies. Groups 4–5 female nude mice can be given injections i.v. through the tail vein with 100 ul of increasing amounts of compound. $LD_{50}$ can be obtained by noting the doses that caused 50% death of animals. Some animals can be examined for tissue toxicity by H/E staining.

In vivo antitumor activity studies can be performed using MDA-231 nude mice xenograft or HRG transfected MCF-7 cells. The appropriate dose schedule and route of treatment for a compound can be determined, starting with the dose of $LD_{10}$.

All publications, patents and patent documents are incorporated by reference herein, as though individually incorporated by reference. The invention has been described with reference to various specific and preferred emnbodiments and techniques. However, it should be understood that many variations and modifications may be made while remaining within the spirit and scope of the invention.

What is claimed is:

1. A therapeutic method to inhibit cancer cell growth comprising administering to a mammal (i.e. a human) in need of such therapy, an amount of a compound of formula (I):

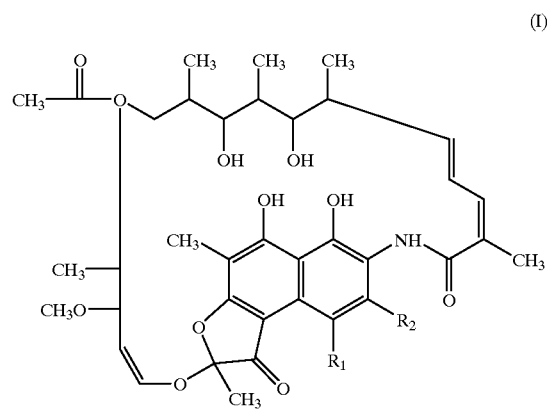

wherein $R_1$ is OH or $-CH_2C(O)N((C_1-C_4)alkyl)_2$;

$R_2$ is $-CH=N-N(R_7)(R_8)$, $-CH=NO((C_1-C_{12})alkyl)$, $-CH=NOCH(phenyl)_2$, $-CH=NO(CH_2)_n$-phenyl, $-CH=N-NHR_9$, $-CH=N-R_{10}$

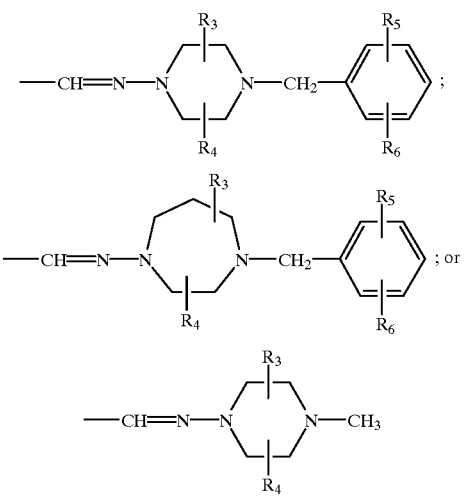

n is 1–6;

$R_3$ and $R_4$ are each independently H, $(C_1-C_4)$alkyl, halo, halo$(C_1-C_4)$alkyl, or $(C_5-C_7)$aryl optionally comprising 1–2 N, S or non-peroxide O and optionally substituted with $(C_1-C_4)$alkyl or halo;

$R_5$ and $R_6$ are each independently H, OH, $-NH_2$, $-C(O)OH$ or $-C(O)NH_2$;

$R_7$ is H or $(C_1-C_4)$alkyl; and $R_8$ is a bi- or tricyclic ring, said ring comprising 7 to 10 carbons, optionally comprising one or more heteroatoms selected from S, N or non-peroxide O, said ring optionally substituted with $(C_{1-4})$alkyl, halo or halo$(C_1-C_4)$alkyl; or $R_7$ and $R_8$ together with the nitrogen to which they are attached form a ring comprising 10 to 20 carbons, optionally comprising one or more heteroatoms selected from S, N or non-peroxide O, said ring optionally substituted with $(C_1-C_4)$alkyl, halo or halo$(C_1-C_4)$alkyl;

$R_9$ is $(C_1-C_4)$alkyl, a peptidyl residue of naturally occurring amino acid, or a di-, tri-, or tetra-peptide; and $R_{10}$ is a a piperazin-1-yl ring, optionally substituted on carbon with one or two substituents selected from the values defined for $R_3$ and $R_4$, and optionally substituted at the 4-position with a group $R_{11}$, wherein $R_{11}$ is $(C_1-C_4)$alkyl, phenyl, benzyl, a peptidal residue of a naturally occuring amino acid, or a di-, tri-, or tetra-peptide;

or a pharmaceutically acceptable salt thereof;

wherein said amount is effective to inhibit growth of said cancer cells.

2. The method of claim 1 wherein the cancer cells are breast cancer cells.

3. A method for antagonizing the actions of a heregulin or its receptor by contacting said receptor with an effective amount of a compound of claim 1.

4. A method for treating a disease or condition in which cell signaling by a heregulin or its receptor(s) is implicated, comprising administering to a mammal afflicted with said disease or condition, an antagonistically effective amount of a compound as described in claim 1.

5. A compound of formula (I)

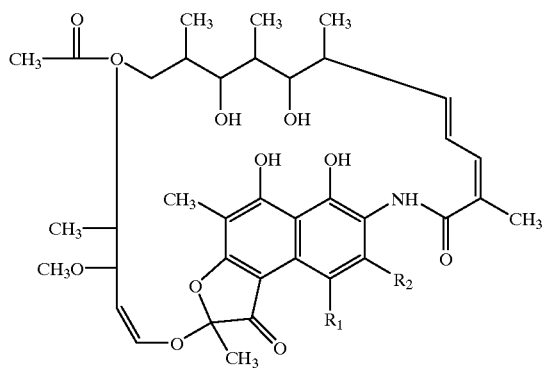

(I)

wherein $R_1$ is OH or —$CH_2C(O)N((C_1-C_4)$alkyl$)_2$;

$R_2$ is —CH=N—N($R_7$)($R_8$), —CH=NO(($C_1-C_{12}$) alkyl), —CH=NOCH(phenyl)$_2$, —CH=NO(CH$_2$)$_n$-phenyl, —CH=N—NHR$_9$, —CH=N—R$_{10}$

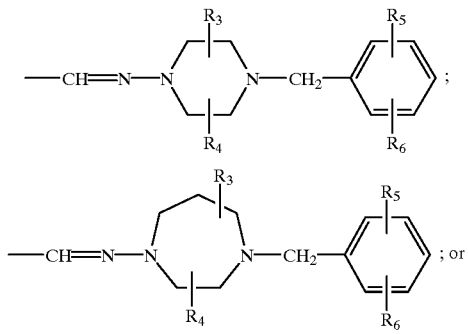

-continued

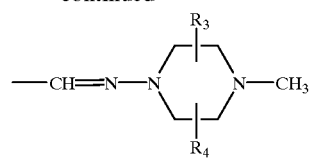

n is 1–6;

$R_3$ and $R_4$ are each independently H, $(C_1-C_4)$alkyl, halo, halo$(C_1-C_4)$alkyl, or $(C_5-C_7)$aryl optionally comprising 1–2 N, S or non-peroxide O and optionally substituted with $(C_1-C_4)$alkyl or halo;

$R_5$ and $R_6$ are each independently H, OH, —NH$_2$, —C(O)OH or —C(O)NH$_2$;

$R_7$ is H or $(C_1-C_4)$alkyl; and $R_8$ is a bi- or tricyclic ring, said ring comprising 7 to 10 carbons optionally comprising one or more heteroatoms selected from S, N or non-peroxide O, said ring optionally substituted with $(C_1-C_4)$alkyl, halo or halo$(C_1-C_4)$alkyl; or $R_7$ and $R_8$ together with the nitrogen to which they are attached form a ring comprising 10 to 20 carbons, optionally comprising one or more heteroatoms selected from S, N or non-peroxide O, said ring optionally substituted with $(C_1-C_4)$alkyl, halo or halo$(C_1-C_4)$alkyl;

$R_9$ is $(C_1-C_4)$alkyl, a peptidyl residue of naturally occuring amino acid, or a di-, tri-, or tetra-peptide; and $R_{10}$ is a a piperazin-1-yl ring, optionally substituted on carbon with one or two substituents selected from the values defined for $R_3$ and $R_4$, and optionally substituted at the 4-position with a group $R_{11}$, wherein $R_{11}$ is $(C_1-C_4)$alkyl, phenyl, benzyl, a peptidal residue of a naturally occuring amino acid, or a di-, tri-, or tetra-peptide;

or a pharmaceutically acceptable salt thereof.

6. A pharmaceutical composition comprising an effective cancer cell growth inhibitory amount of a compound of claim 5, in combination with a pharmaceutically acceptable carrier.

7. The compound of claim 5 wherein $R_2$ is —CH=N—N($R_7$)($R_8$) or —CH=NO(CH$_2$)$_n$-phenyl.

8. The compound of claim 5 wherein $R_2$ is —CH=N—NHR$_9$.

9. The compound of claim 5 wherein $R_1$ is OH.

10. The compound of claim 5 wherein $R_2$ is

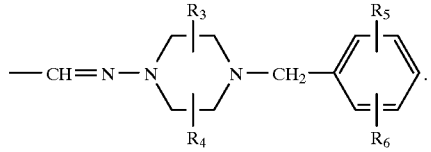

* * * * *

UNITED STATES PATENT AND TRADEMARK OFFICE
CERTIFICATE OF CORRECTION

PATENT NO.: 6,143,740

DATED: Nov. 07, 2000

INVENTOR(S): Yang et al.

It is certified that errors appear in the above-identified patent and that said Patent is hereby corrected as shown below:

In column 12, line 57 delete "$(C_{1-4})$" and insert -- $(C_1 - C_4)$ --, therefor.

Signed and Sealed this

First Day of May, 2001

Attest:

NICHOLAS P. GODICI

*Attesting Officer*    *Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,143,740 | Page 1 of 1 |
| APPLICATION NO. | : 09/308396 | |
| DATED | : November 7, 2000 | |
| INVENTOR(S) | : Yang et al. | |

It is certified that error appears in the above-identified patent and that said Letters Patent is hereby corrected as shown below:

Column 1, Line 6, please insert the paragraph: "Work herein was funded, in whole or in part, by the Department of the Army Grant # DAMD17-99-1-9208. The United States government has certain rights in the invention."

Signed and Sealed this

Twenty-fourth Day of October, 2006

JON W. DUDAS
*Director of the United States Patent and Trademark Office*